United States Patent [19]
Esposito et al.

[11] 3,970,427
[45] July 20, 1976

[54] PROCESS FOR REDUCING STICKING OF BLOOD CELLS TO GLASS IN BLOOD TESTING PROCEDURES

[75] Inventors: Vito M. Esposito; Stanley B. Weinstein, both of Miami, Fla.

[73] Assignee: American Hospital Supply Corporation, Evanston, Ill.

[22] Filed: Mar. 22, 1973

[21] Appl. No.: 343,973

[52] U.S. Cl. .............................. 23/230 B; 252/408
[51] Int. Cl.$^2$ ................. G01N 33/16; G01N 31/00
[58] Field of Search .................. 23/230 B; 252/408; 424/11, 12

[56] References Cited
UNITED STATES PATENTS
3,677,710    7/1972    Hirsch .............................. 424/12 X OTHER PUBLICATIONS
Medicinal Chemistry, 3rd ed, Pt. II, Wiley–Interscience, N.Y. (1971), pp. 1185–1188.
Chem. Abstr., vol. 65:6064h (1966).
Chem. Abstr., vol. 74:29993q (1971).
Gradwshl's Clinical Lab Methods & Diagnosis, vol. 1, pp. 717–718 (1970).
Martindale: The Extra Pharmacopoeia, Pharmaceutical Press, London (1972); pp. 1079–1080 and 1715.
Chem. Abstr., vol. 73:118564x (1970).
U.S. Dispensatory, 26th ed., pp. 532–533 (1967).

*Primary Examiner*—Morris O. Wolk
*Assistant Examiner*—Timothy W. Hagan
*Attorney, Agent, or Firm*—Dawson, Tilton, Fallon & Lungmus

[57] ABSTRACT

Blood Cells are suspended in a physiological saline solution modified by the addition of a small amount of gelatin. The presence of gelatin serves to reduce attractive forces between the blood cells and glass surfaces in testing procedures.

3 Claims, No Drawings

PROCESS FOR REDUCING STICKING OF BLOOD CELLS TO GLASS IN BLOOD TESTING PROCEDURES

BACKGROUND

Dilutions or suspensions in serological tests are commonly made with a 0.85 percent (0.15M) solution of sodium chloride, usually referred to as physiological or isotonic saline, Thus, in blood grouping tests, erythrocytes of the donor (or recipient) are first suspended in a small amount of physiological saline and the suspension is then mixed with a serum known to agglutinate blood of one type or another. After centrifugation, a small button of sedimented cells appears at the bottom of the tube. Gentle shaking of the tube then reveals whether agglutination has or has not occurred. If the cells disperse and resuspend uniformly, the results are negative; if instead the button dislodges from the wall of the tube but remains in the form of one or more relatively large clumps which are not broken up by shaking, then agglutination has occurred and the results are positive.

While there are many variations of the above procedure, depending on the particular tests being conducted, the step of agitating an aggregation of cells to observe their tendency to resuspend in saline is common to most of them, whether such step takes place in a centrifuge tube or on a microscope slide. A problem frequently arises when the mass of cells neither disperses nor releases as an aggregate but instead adheres firmly to the glass surface. If cells remain in place despite such agitation, then the serologist cannot be certain whether the resistance to dispersion arises because of agglutination or simply because of the tendency of the cells to stick to the glass. On the other hand, if a probe or excessive agitation should be used to dislodge the button from the glass, and should the cells then resuspend, there may be uncertainty as to whether such resuspension occurred because of a true negative reaction or because the mechanical force applied to the button caused the agglutinated cells of a positive test to separate. Therefore, the attraction between blood cells and glass surfaces, a well known phenomenon in clinical labroatories, has created problems which have tended to complicate blood testing procedures and to effect their accuracy and reliability. Despite the long-standing nature of such problems, no effective solution has heretofore been developed.

SUMMARY

A main aspect of the present invention lies in the discovery that the aforementioned problems may be eliminated or reduced if the physiological saline used in such blood testing procedures is modified to include a small amount of gelatin. For reasons not yet fully known, the inclusion of gelatin reduces hemolysis of erythrocytes and eliminates or greatly reduces the problem of sticking between erythrocytes and glass surfaces described above. In general, the modified saline preparation is believed superior in any instance where physiological saline has heretofore been required for in vitro blood bank procedures, including washing and prepartion of erythrocyte suspensions, direct antiglobulin tests, indirect antiglobulin tests, major and minor compatibility tests, blood grouping and typing, antibody screening and identification, and tests utilizing enzyme methods.

DESCRIPTION

The aqueous sodium chloride solution must be sterile and isotonic, as in a standard physiological saline solution. Specifically, the sodium chloride concentration should be within the range of 0.80 to 0.90 percent, the optimum level being 0.85 percent (0.15 Molar). The concentration of gelatin should in general fall within the range of 0.001 to 2.0 percent by weight (grams per 100 milliliters) and preferably within the range of 0.001 to 1.0 percent. Effectiveness diminishes with lower concentrations whereas higher concentration levels might present reflectance problems and might provide some support for microbial growth without significant increase in effectiveness. For immunohematological testing, the optimum concentration appears to be approximately 0.1 percent.

Gelatin suitable for use in connection with this invention should be in finely divided form to facilitate dissolving in saline and should be of at least laboratory grade purity in accordance with the listing in the U.S. Pharmacopeia or National Formulary.

The source of the gelatin and the procedures used in its preparation do not appear critical. Thus, gelatin obtained from the partial hydrolysis of collagen derived from calfskin, pigskin, and the skin, white connective tissue, and bones of various animals all appears suitable. Similarly, the gelatin may be derived from an acid-treated precursor (Type A) or from an alkali-treated precursor (Type B). For the uses contemplated by this invention, the gelatin-saline solution would be prepared and packaged in sterile condition; however, some preservatives may be desirable, especially if the product is to be stored for any length of time in the laboratory after the container has once been opened. Any suitable preservatives or antibacterial agents such as neomycin sulfate and chloramphenicol may be used.

No special or unusual procedures are required for preparation of the modified physiological saline except that the final step in any commercial production must include sterilization. Sterile filtration has been found particularly effective. Also, since gelatin is insoluble or only slightly soluble in cold water, the water or saline used in preparing the solution must be heated moderately to dissolve the gelatin particles.

The precise reasons why the inclusion of gelatin so significantly increases the effectiveness of physiological saline in blood testing procedures are not known, partly because the precise mechanism of erythrocyte agglutination has never been fully known. It is conceivable that gelatin has some effect in reducing cell charge differences, or in reducing surface tension of the suspending medium (i.e., the modified saline). Since the performance in agglutination reactions is so noticeably superior to that of standard (unmodified) physiological saline, it might reasonably be concluded that some enhancement of the reaction has occurred; however, to fully explain such action, more complete information concerning the mechanism of erythrocyte agglutination must become available.

Parallel studies of standard physiological saline and modified physiological saline have shown that less hemolysis occurs when erythrocytes are washed and suspended in the modified saline, cell buttons are more easily suspended and are better delineated in the modified saline, the stickiness of erythrocytes, particularly with respect to glass surfaces, is greatly reduced when the modified saline is used, the rough appearance of cells under the microscope in Coombs testing is eliminated or greatly reduced when modified saline is used, and antibody screening and identification is enhanced when modified saline is used, the reactions being easier to read and more reproducible.

The invention and its advantages may be more fully understood from the following illustrative examples:

EXAMPLE 1

Modified physiological saline was prepared in accordance with the present invention using the following reagents and concentrations:

| Reagents | Concentration (W/V) |
|---|---|
| Sodium Chloride, certified A.C.S. (Fisher Scientific Company, Fair Lawn, New Jersey) | 0.85% |
| Gelatin, Granular, laboratory grade (G-7, Fisher Scientific Company, Fair Lawn, New Jersey) | 0.1% |
| Neomycin Sulfate (Pfizer, Inc., Chamblee, Georgia) | 0.03% |
| Chloramphenicol (Parke, Davis and Company, Detroit, Michigan) | 0.02% |
| Distilled Water | |

Stock solutions of each of the reagents were prepared. Thirty grams of the sodium chloride crystals were dissolved in 100 milliliters of distilled water to make up the sodium chloride stock solution. Stock solutions of neomycin sulfate and chloramphenicol were similarly prepared using 10 grams per 100 milliliters for the neomycin sulfate solution and 0.44 grams per 100 milliliters for the chloramphenicol solution. A 10 gram percent concentrate of gelatin was prepared by heating the distilled water to 50° C. before addition of the gelatin. After addition of the gelatin, the constituents were stirred for 10 minutes at 50° C. to effect complete solution.

Thereafter, the following volumes from the respective stock solutions were mixed together and distilled water was then added to produce a final volume of one liter: 28.3 ml sodium chloride stock solution; 10.0 ml gelatin stock solution; 3.0 ml neomycin sulfate stock solution; 45.5 ml chloramphenicol stock solution. The final product was stored at 4° C. until sterile filtration which was undertaken within 24 hours following preparation of the solution.

Similar solutions of modified physiological saline were prepared using gelatin of other grades and sources, such as gelatin 1099 (purified calfskin), gelatin 5247 (purified pigskin), and gelatin G-8 (granular, laboratory grade, 270 bloom), all obtained from Fisher Scientific Company, Fair Lawn, New Jersey, and gelatin G-2500 (swine skin, type 1, approximately 300 bloom), obtained from Sigma Chemical Company, St. Louis, Missouri. All produce substantially the same results with the laboratory grade gelatin being generally as effective as the more purified forms. Also, elimination of the preservatives (neomycin sulfate and chloramphenicol) did not adversely affect the results as long as the modified physiological saline was used shortly after preparation or shortly after its sterile package has been opened.

EXAMPLE 2

Over 100 test suspensions of 3 to 5 percent (V/V) of human erythrocytes were prepared using the modified physiological saline of Example 1 and were visually compared with a like number of test suspensions in which conventional physiological saline was used. The suspensions were maintained for varying periods up to about 21 days and were observed for hemolysis and general appearance of the erythrocytes. Free hemoglobin and moderate aggregation of erythrocytes were observed in the suspensions of conventional physiological saline. In marked contrast, the modified physiological saline suspensions were devoid of free hemoglobin and the erythrocytes remained in non-aggregated condition.

EXAMPLE 3

ABO grouping and Rh-Hr typing of erythrocytes were performed to compare delineation of cell buttons and ease of suspension of cells in normal (conventional) and modified physiological saline. Multiple suspensions of erythrocytes were prepared in both solutions and tests were performed in accordance with the instructions of anti-serum manufactures. manufacturers. typical procedure involved the preparation of a 2 percent (V/V) suspension of washed red cells in the saline (either normal physiological saline or modified physiological saline), and thereafter placing one drop of the cell suspension in a small test tube to which was then added one drop of anti-serum. The contents of the tube were then mixed by agitation and were centrifuged, typically for one minute at 1,000 rpm (RCF 125g), or for 20 seconds at 3,400 rpm (RCF 1,000g). The tube was then removed from the centrifuge and gently shaken, after which its contents were examined macroscopically for agglutination. Microscopic examination was also undertaken.

In those tests in which the cells were suspended in normal (conventional) physiological saline, the cell buttons appeared diffuse and grainy and were characteristically accompanied by a halo or faint ring on the inside surface of the tube. The buttons did not release readily in positive tests and in most instances the ring or halo was left on the inside surface of the tube when resuspension did occur. In contrast, the tests in which modified physiological saline was used (prepared as set forth in Example 1) resulted in a cell button which appeared compact, smooth, resilient, and well defined. Even in positive tests the button was dislodged readily; in most instances, the button released from the bottom of the tube at the same time that the tube was lifted free from the centrifuge. The ring or halo observed in connection with the tests using normal physiological saline was not observed in the tests using modified physiological saline prepared in accordance with Example 1.

EXAMPLE 4

In addition to tube methodology for blood grouping and typing, the reactions may, in some instances, be performed on glass slides. The stickiness of erythrocytes for glass can be demonstrated by placing the cells on the glass slide for a few seconds and then tilting the slide so that the cells will drain off of the glass surface.

Using the above procedure, erythrocyte suspensions (5% V/V) were prepared using normal (conventional) physiological saline and were then placed on slides as described. After the cells had drained off of the tilted slide, an opaque or transulucent residue remained, indicating the presence of a substantial number of cells still adhering to the glass. Repeating the same test using modified physiological saline prepared as set forth in Example 1, the macroscopic observation was that the residue was far less opaque (more transparent). Microscopic examination confirmed that relatively few cells remained upon the glass surface when modified physiological saline was used in comparison with the cells retained when conventional physiological saline was employed.

EXAMPLE 5

Tests reveal that antigen-antibody reactions are more reproducible using modified physiological saline of Example 1 than using normal (conventional) physiological saline. In a series of identical antigen-antibody tests performed in modified and normal saline, stronger reactions were commonly observed in the modified saline tests. Using the scheme of grading the strength of agglutination reactions commonly in use (as set forth in Technical Methods and Procedures of the American Association of Blood Banks, page 47, 5th Edition, 1970), a substantial proportion of tests reported as 1+ reactions with normal saline were reported as 2+ or stronger reactions using the modified saline of the present invention. The increased reactivity resulted in more reproducible tests, especially with weak or low concentrations of antibody. Microscopic readings confirmed the macroscopic observations.

While in the foregoing we have disclosed an embodiment of the invention in considerable detail for purposes of illustration, it will be understood by those skilled in the art that many of such details may be varied without departing from the spirit and scope of the invention.

We claim:

1. A blood testing procedure in which blood cells are disposed in close relation to glass surfaces, comprising the step of suspending said cells in a sterile physiological saline solution containing gelatin in a concentration range of approximately 0.001 to 2.0 percent, said gelatin being effective to reduce attraction forces between said blood cells and said glass surfaces.

2. A blood testing procedure in which blood cells are disposed in close relation to glass surfaces, comprising the step of suspending said cells in a sterile physiological saline solution containing gelatin in a concentration range of approximately 0.001 to 1.0 percent, said gelatin being effective to reduce attraction forces between said blood cells and said glass surfaces.

3. The procedure of claim 2 in which the concentration of gelatin is approximately 0.1 percent.

* * * * *